(12) United States Patent
Pontoppidan et al.

(10) Patent No.: US 9,555,243 B2
(45) Date of Patent: Jan. 31, 2017

(54) CALIBRATION METHOD FOR COCHLEAR SYSTEM AND HEARING SYSTEM APPLYING CALIBRATION MAPPING

(71) Applicant: Oticon Medical A/S, Smørum (DK)

(72) Inventors: Niels Henrik Pontoppidan, Smørum (DK); Morten Eduard Hartvig, Smørum (DK); Filip Marchman Rønne, Smørum (DK)

(73) Assignee: OTICON MEDICAL A/S, Smørum (DK)

( * ) Notice: Subject to any disclaimer, the term of this patent is extended or adjusted under 35 U.S.C. 154(b) by 0 days.

(21) Appl. No.: 14/792,009

(22) Filed: Jul. 6, 2015

(65) Prior Publication Data

US 2016/0001077 A1  Jan. 7, 2016

(30) Foreign Application Priority Data

Jul. 4, 2014  (EP) .................................... 14175841

(51) Int. Cl.
| | | |
|---|---|---|
| A61N 1/36 | (2006.01) | |
| A61B 5/00 | (2006.01) | |
| A61B 5/12 | (2006.01) | |
| A61N 1/08 | (2006.01) | |
| A61N 1/05 | (2006.01) | |
| H04R 25/00 | (2006.01) | |

(52) U.S. Cl.
CPC .......... *A61N 1/36032* (2013.01); *A61B 5/125* (2013.01); *A61B 5/686* (2013.01); *A61B 5/6817* (2013.01); *A61N 1/0541* (2013.01); *A61N 1/08* (2013.01); *H04R 25/70* (2013.01); *H04R 2225/67* (2013.01)

(58) Field of Classification Search
None
See application file for complete search history.

(56) References Cited

U.S. PATENT DOCUMENTS

| | | | |
|---|---|---|---|
| 4,207,441 A | 6/1980 | Ricard et al. | |
| 4,532,930 A | 8/1985 | Crosby et al. | |
| 5,061,282 A | 10/1991 | Jacobs | |
| 5,344,387 A * | 9/1994 | Lupin .................. | H04R 25/606 181/130 |
| 5,856,722 A * | 1/1999 | Haronian ................. | H03H 9/50 310/309 |
| 2001/0049466 A1* | 12/2001 | Leysieffer .......... | A61N 1/36032 600/25 |
| 2002/0138115 A1* | 9/2002 | Baumann ........... | A61N 1/36032 607/57 |
| 2003/0012390 A1* | 1/2003 | Franks ............... | A61N 1/36032 381/114 |
| 2003/0167077 A1* | 9/2003 | Blamey .............. | A61N 1/36032 607/57 |

(Continued)

FOREIGN PATENT DOCUMENTS

WO  WO 2010/068984 A1  6/2010

*Primary Examiner* — Kennedy Schaetzle
(74) *Attorney, Agent, or Firm* — Birch, Stewart, Kolasch & Birch, LLP

(57) ABSTRACT

The present disclosure relates to a method of calibrating a cochlea implant and present disclosure relates to a cochlea implant. Further, the present disclosure relates to use of cochlea implants and use of calibration method for cochlea implants. The methods, uses, and implants of the present disclosure provides improved auditory experience for the users of cochlea implants.

18 Claims, 2 Drawing Sheets

(56) References Cited

U.S. PATENT DOCUMENTS

| | | |
|---|---|---|
| 2006/0052841 A1 | 3/2006 | Daly et al. |
| 2006/0100672 A1 | 5/2006 | Litvak |
| 2006/0178711 A1* | 8/2006 | Patrick ............... A61N 1/36032 607/57 |
| 2011/0112355 A1* | 5/2011 | Van den Heuvel ............. A61N 1/36032 600/25 |
| 2014/0194673 A1* | 7/2014 | Goldenberg ......... H04R 25/608 600/25 |

* cited by examiner

Fig. 5
Fig. 4
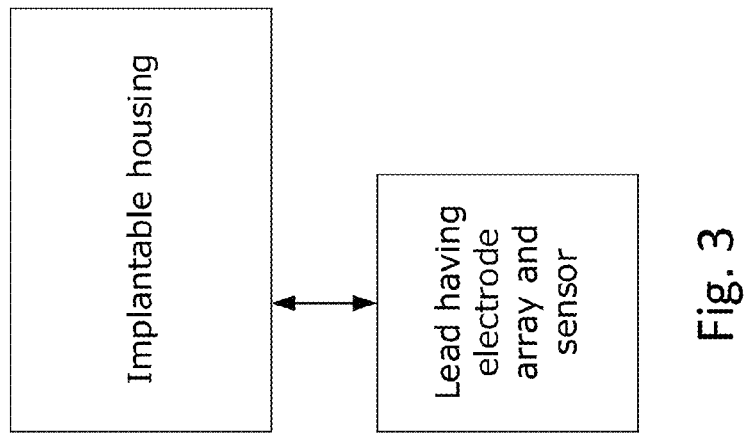
Fig. 3
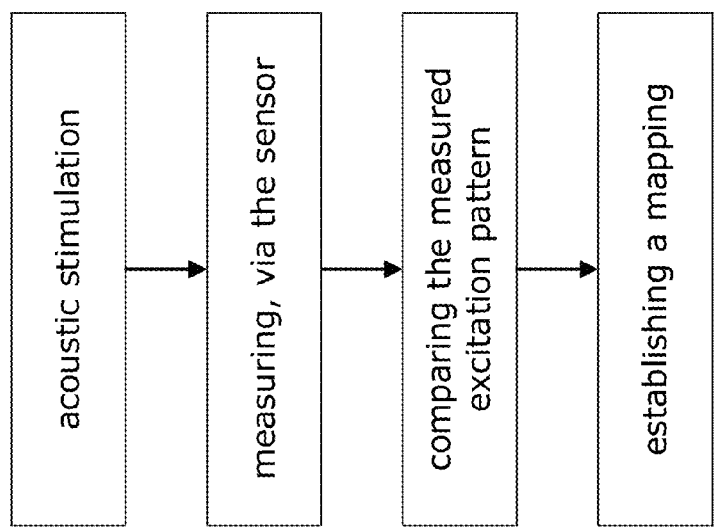
Fig. 2

CALIBRATION METHOD FOR COCHLEAR SYSTEM AND HEARING SYSTEM APPLYING CALIBRATION MAPPING

FIELD OF THE DISCLOSURE

The present disclosure relates to a hearing system and a method for operating a hearing system. In particular, the disclosure relates to a cochlea hearing system and a method of operating a cochlea hearing system.

BACKGROUND

Cochlea implants use digital signal processing techniques to decompose an input signal into multiple frequency-filtered bands, which are then transmitted to an electrode array implanted in the scala typmani for direct stimulation thereof. While cochlea implants do deliver significant auditory functionality to patients with profound hearing loss, there are still problems with the cochlea implants.

For a healthy ear with functioning cochlea, there is a tonotopic mapping from frequencies in the sound signal that excites the round window to the place of excitation on the cochlea, and further to the auditory nerves that converts the motion of the basilar membrane at that point to nerve signals.

The cochlea performs the function of frequency dispersion by causing sound input at certain frequencies to vibrate at some locations and other frequencies to vibrate at other locations on the basilar membrane. It has been shown that high frequencies lead to maximum vibrations at the basal end of the cochlea coil and low frequencies lead to maximum vibration at the apical end and stimulation of the nearby auditory cells. The tonotopic organisation of the basilar membrane is therefore followed by a tonotopic organisation of the auditory nerves, which means that a given auditory nerve is associated with the frequency corresponding to its position on the basilar membrane.

When implanting the electrode array in the scala typmani the frequency mapping that associates each electrode with the frequency corresponding to the nearest auditory nerve is not known due to variations in length of basilar membrane, insertion depth, etc.

Cochlea implant bypasses the middle ear, basilar membrane and stimulates the auditory nerves directly. This means that electric signals may be transferred directly or indirectly to cochlear nerve and/or to auditory cortex of the user. Hence, the aforementioned tonotopic mapping provided by the basilar membrane is not available for cochlea implants, as the sound is not converted to nerve signals by the ear.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing device comprises multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

For end-users with unilateral deafness, pitch mapping and other objective measures such as ASSR, can be used to obtain the mapping from acoustic frequency to electrode position. However, that is not possible for bilateral deafness as there is no healthy reference to which the mapping can be compared to.

Hence, an improved cochlea hearing system, in particular suitable for bilateral deaf people, further an improved method of operating a cochlea hearing system, would be advantageous. Bilateral deaf people may e.g. have two implants, one at each cochlea.

It is a further object of the present disclosure to provide an alternative to the prior art.

In particular, it may be seen as an object of the present disclosure to provide a cochlea hearing system and/or method for operating a cochlea hearing system, that solves, at least alleviates or provides an alternative the above mentioned problems of the prior art.

SUMMARY

Thus, the above-described object and several other objects are intended to be obtained in a first aspect by providing a calibration method including establishing a calibration mapping for calibrating a hearing system comprising a cochlea implant having a lead including an electrode array and a plurality of sensors configured to sense vibrations of the basilar membrane while in an implanted state. The output from the sensors is preferably only recorded during a calibration phase. The sensors are preferably not used as microphones during normal operation. The method may comprise providing acoustic stimulation in the ear canal with an acoustic test signal with known spectrum, where after the middle ear converts the acoustic test sound to mechanical excitation of the basilar membrane, which responds with motion that performs a frequency-to-place conversion. The method may comprise measuring, via the sensor in the cochlea implant, the excitation pattern of the basilar membrane. The method may comprise comparing the measured excitation pattern of the basilar membrane with an expected excitation pattern based on the acoustic test signal. The expected excitation pattern may be established based on previous measurements and/or a model or simulation of the cochlea. The method may comprise establishing a mapping by assigning characteristic frequencies to the excitated positions and the electrode array.

In a second aspect, the present disclosure provides a cochlea implant including an implantable housing having a lead configured to be implanted into the cochlea of a user. The cochlea implant may include the lead including an electrode array and a plurality of sensors. The processor may store a calibration mapping that assigns characteristic frequencies to the excitated positions of the electrode array relative to the cochlea when in an implanted state. The cochlea implant may include a processor configured to receive an input signal to be presented to the user via the electrode array. The processor may be configured to apply a calibration mapping so as to achieve stimulation of the cochlea according to the calibration mapping when presenting the input signal to the usercochlea.

Further features of the aspects are apparent from the detailed description of the figures below.

The individual features of each aspect may each be combined with any or all features of the other aspects. These and other aspects, features and/or advantages will be apparent from and elucidated with reference to the embodiments described hereinafter.

BRIEF DESCRIPTION OF THE FIGURES

The apparatus/method will now be described in more detail with regard to the accompanying figures. The figures illustrates exemplary implementations and is not to be construed as being limiting to other possible embodiments falling within the scope of the attached claim set.

FIG. 2 schematically illustrates steps of a method,

FIG. 3 schematically illustrates an implant housing and a lead, and

FIGS. 4 and 5 schematically illustrates sections of leads with electrodes and sensors.

DETAILED DESCRIPTION OF AN EMBODIMENT

Figure 1:
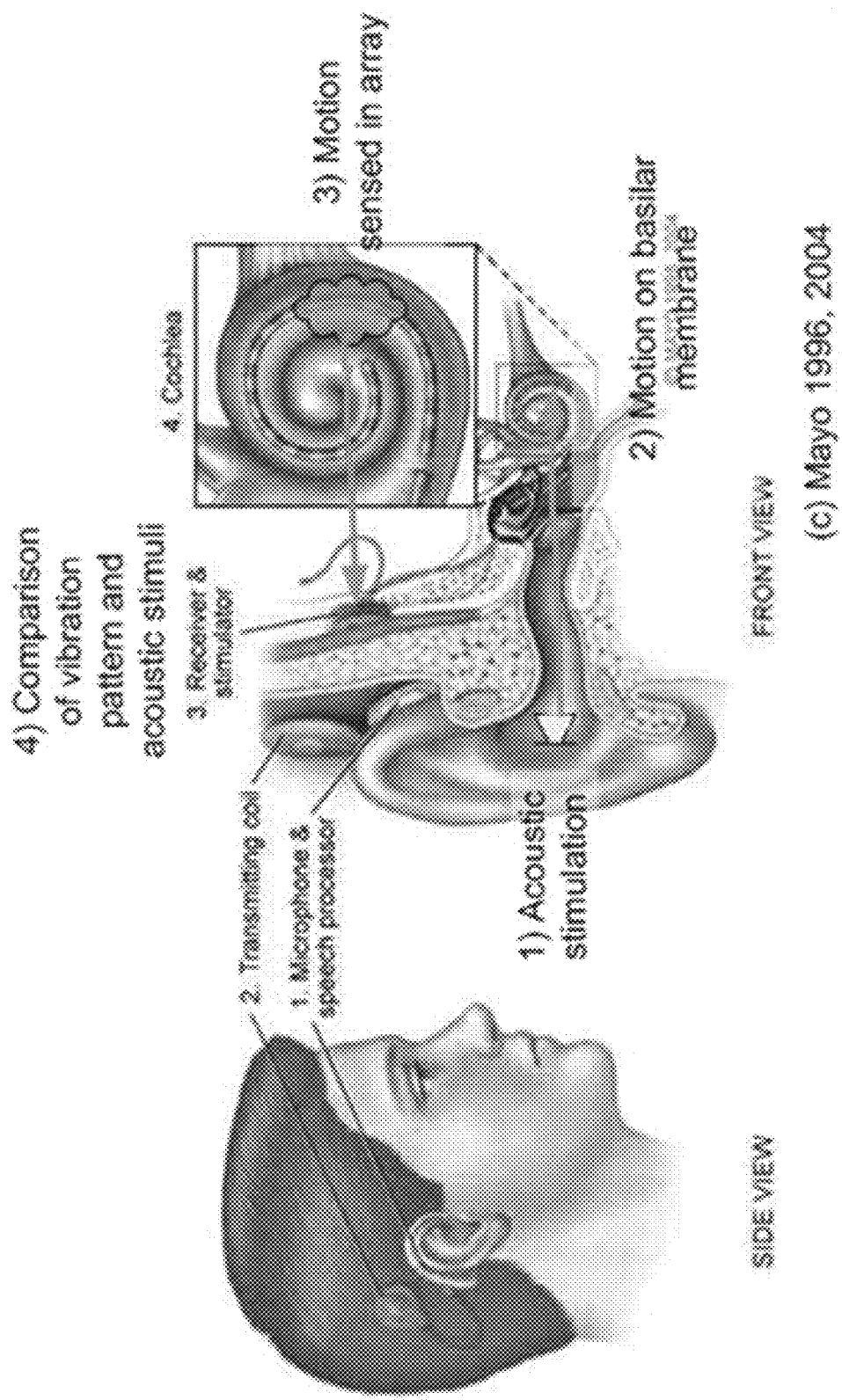
FIG. 1 schematically illustrates a user having a cochlea implant.

The figures are schematic and simplified for clarity, and they just show details to improve the understanding of the claims, while other details are left out. Throughout, the same reference numerals are used for identical or corresponding parts.

FIG. 1 schematically illustrates a user with a cochlea implant, seen in a side view on the left side of FIG. 1. In the right side of FIG. 1 a sectional view of the ear of the user is illustrated. Here an implant-part is located on the inside of the skull with an inductive link to an external transmitter placed on the skin of the user. A lead is connected to the implant-part and extends into the cochlea via the oval window in a usual manner into one of the scala. The lead includes, besides electrodes, sensors for sensing vibrations. The sensors are configured to picking up vibrations generated by the cochlea. The sensors are not used as microphones during normal use of the cochlea implant.

When a lead of a cochlea implant is inserted into the cochlea to provide a stimulus to the user, the relative position of the electrodes of the lead and the wall of the cochlea is not a fixed, known relation. The plurality of electrodes stimulate respective areas of the cochlea in order to provide a hearing sensation to the user suffering from sensorineural deafness. Each electrode is electronically independent from adjacent electrode, and, therefore, can generate localized electrical impulses along the entire length of the cochlea as a result. As the electrodes stimulate the area or region of the cochlea in which they are located, a calibration of the output signal is advantageous. This is contemplated to provide a better sound experience for the user, as, as explained above, different frequencies are picked up at different positions in the cochlea. By having a knowledge of the frequency or frequency range picked up by the particular area or section of the cochlea near a specific electrode of the lead, a better sound experience may be provided to the user.

A calibration method may be performed initially when the user has had the surgery for positioning the implant. Further, calibration method may be performed at any point in time, e.g. on a regular basis autonomously by the system. The calibration may also be executed by a system supervised by a health care professional, e.g. when the user visits an ENT.

The calibration includes a step of a tone being played in the ear canal. This acoustic stimulation excites the basilar membrane through the middle ear and results in motion of the basilar membrane at the place with matching characteristic frequency. The calibration method includes a step of sensing the motion of the basilar membrane and/or other parts of the cochlea by the sensors in the electrode array. The calibration method includes a step of comparing the excitation pattern to the frequencies in the acoustic stimulation. The calibration method includes a step of estimating which electrodes match the excitation pattern. This allows a calibration set to be established. This calibration set may then be applied to a signal before it is supplied to the electrodes for stimulation of the cochlea.

The calibration method utilizes the remaining mechanical functioning of the damaged ear. The hearing impairment or deafness that the cochlea implant treats originates from the situation that the acoustic sound is not converted correctly, or at all, to auditory nerve impulses. However, the basilar membrane, and thereby also other parts of the cochlea, will still respond with motion to the incoming sound, causing specific vibrational patterns. The electrode array is sensitive to the motion on the basilar membrane, owing to the suitable sensors, and may therefore match the motion patterns with the frequencies in the sound.

An exemplary set of method steps may include:

Step 1: Acoustic stimulation in the ear canal with a signal with known spectrum, here a 1 kHz tone. This step may include providing a broadband signal with a range of frequencies, or multiple signals with discrete tones or intervals of tones or frequencies.

Step 2: The middle ear converts the acoustic sound to mechanical excitation of the basilar membrane, which responds with motion that performs a frequency to place conversion.

Step 3: The sensors in the electrode array measure the excitation pattern of the basilar membrane.

Step 4: The cochlea implant processor compares the excitation pattern of the basilar membrane with the excitation pattern that the acoustic stimulation in step 1 would generate, and hereby establishes the mapping that assigns characteristic frequencies to the excitated electrode positions.

Other suitable frequencies may be used. The duration of the stimulation may be in the range from a few milliseconds to several seconds. The sound pressure level should be sufficient for the sensors to register vibrations.

Filtering the sensor signal, e.g. to reduce or eliminate unwanted vibrations from other parts of the body or from external sources, may improve registration of the vibrations For unilateral deafness pitch-matching is an option, however it is not very accurate. Moreover, the acoustic reference pitch is not present for bilateral deafness. The disclosed method would allow the cochlea implant to stimulate at the frequencies that the ear was expecting.

FIG. 2 schematically illustrates a method of calibrating a hearing system comprising a cochlea implant having a lead including an electrode array and a plurality of sensors configured to sense vibrations of the basilar membrane while in an implanted state.

The method comprises a step of acoustic stimulation in the ear canal with an acoustic test signal with known spectrum, where after the middle ear converts the acoustic test sound to mechanical excitation of the basilar membrane, which responds with motion that performs a frequency-to-place conversion. The method comprises a step of measuring, via the sensor in the cochlea implant, the excitation pattern of the basilar membrane. The method comprises a step of comparing the measured excitation pattern of the basilar membrane with an expected excitation pattern based on the acoustic test signal. The expected excitation pattern may be based on a model of the cochlea, indicating positions where frequency bands or specific frequencies are usually registered in the cochlea. The expected excitation pattern may be updated by one or more previous measurements, and new measurements, so that movement of the electrode may be compensated. This movement of the electrode could be caused e.g. by growth of the head. In an initial step, e.g. short time after placing the electrode or after replacing a part of the system such as an external unit comprising an input transducer and sound processing unit, a first measurement is performed so as to calibrate the output to the electrode. Some of the electrode array may be in a position not inside the cochlea, and these parts could be mapped so as not to be significantly excited when applying an output signal to the electrode array. The method comprises a step of establishing a mapping that assigns characteristic frequencies to the excited positions.

This calibration, or mapping, of the electrodes ensures an improved auditory sensation of the user, as the implant is able to provide a stimulus signal to the cochlea at positions, which are sensitive to the actual stimulus of the corresponding electrode of the electrode array. When the lead with the electrode array is placed in the cochlea, it is not placed at the exact same position in each individual, also, no two users have exactly the same damage to the cochlea.

As explained herein, the sensor may be any one of a vibration sensor, an accelerometer, or an ultrasound sensor. When using such sensors, the method may comprise obtaining a frequency response from the sensor or sensors.

As more sensors may be needed along the length of the lead, the sensor may comprise a plurality of sub-sensors. These sub-sensors may then be arranged along a length of the lead of the cochlea implant. The method may then comprise obtaining from each of the sub-sensors a signal in response to the acoustic signal, and the step of establishing the mapping may then include mapping the response of each of the sub-sensor's position. Using more sensors provides at least an improved resolution of the mapping.

The hearing system may comprise a processor for processing an input signal, this input signal may be a microphone signal from a device placed on the user, e.g. in a microphone clip or a behind-the-ear device, or other suitable device. The input signal is provided to the implant, e.g. via an inductive link, and the method may then include calibrating the input signal using the processor before applying the processed signal to the electrode array.

The electrodes of the electrode array may be distributed evenly over a length of the lead. There may be areas of the lead where the electrodes are placed more close, so that at least one group of closely spaced electrodes are established.

The plurality of sensors may distributed among the electrodes of the electrode array, e.g. interleaved so that one or more electrodes are positioned between neighboring sensors. Also, more than one sensor may be placed adjacent each other.

FIG. 3 schematically illustrates a cochlea implant including an implantable housing having a lead configured to be implanted into the cochlea of a user. The lead includes an electrode array and a plurality of sensors. The cochlea implant includes a processor configured to receive an input signal to be presented to the user via the electrode array. The processor is configured to apply a mapping of the electrodes of the electrode array to relative positions of the cochlea when in an implanted state. This allows providing an improved auditory experience to the user, as the areas of the cochlea where the electrodes are positioned will be more sensitive to the provided signal.

The electrodes of the electrode array may be distributed evenly over a length of the lead, or the electrodes of the electrode array may include one or more groups of two or more closely spaced electrodes.

The plurality of sensors are distributed among the electrodes of the electrode array, and the cochlea implant includes a processor configured to receive the signals from the plurality of sensors that reflect the mechanical vibration of the Basilar membrane in response to the sound presently presented to the wearers ear. Furthermore, the plurality of sensors may be interleaved with the electrodes of the electrode array, e.g. the lead may include a number of sequences with one electrode and one sensor, or one or more sequences of two electrodes and one sensor, so as to establish a pattern of two electrodes followed by one sensor, again followed by two electrodes etc.

FIG. 4 schematically illustrates a section of a lead where electrodes, illustrated with diagonal lines, and sensor, illustrated with vertical lines, are distributed evenly over a length of the lead.

FIG. 5 schematically illustrates a section of a lead where electrodes, illustrated with diagonal lines, and sensor, illustrated with vertical lines, are grouped in sequences of two electrodes and one sensor over.

The present disclosure also provides use of a mapping of positions of an array of electrodes of a lead of a cochlea implant for providing a signal to a user that the user may perceive as sound, wherein the mapping is a tonotopic mapping of acoustic frequencies to auditory nerve frequencies.

The present disclosure also provides use of a cochlea implant as disclosed herein using a method as disclosed herein.

Combinations of the above embodiments and many other embodiments will be apparent to those of skill in the art upon reading and understanding the above description.

The apparatus and/or method steps as set out in the claims may be implemented by means of hardware, software, firmware or any combination of these. Some of the features could also be implemented as software running on one or more data processors and/or digital signal processors.

The individual elements of any of the disclosed embodiments may be physically, functionally and logically implemented in any suitable way such as in a single unit, in a plurality of units or as part of separate functional units. It is intended that the structural features of the devices described above, in the detailed description and in the claims may be combined with steps of the method, when appropriately substituted by a corresponding process. Embodiments of the method have the same advantages as the corresponding systems.

Although the present disclosure discusses specific embodiments, the claims should not be construed as being in any way limited to the presented examples. Although specific embodiments have been illustrated and described herein, it will be appreciated by those of ordinary skill in the art, that any arrangement which is calculated to achieve the same purpose may be substituted for the specific embodiments shown. The scope of protection is defined by the accompanying claim set. In the context of the claims, the

The invention claimed is:

1. A calibration method including establishing a calibration mapping for calibrating a hearing system comprising a cochlea implant having a lead including an electrode array and a plurality of sensors configured to sense vibrations of the basilar membrane while in an implanted state, the calibration method comprising:
   providing acoustic stimulation in the ear canal with an acoustic test signal with known spectrum, where after the middle ear converts the acoustic test sound to mechanical excitation of the basilar membrane, which responds with motion that performs a frequency-to-place conversion,
   measuring, via the sensor in the cochlea implant, the excitation pattern of the basilar membrane,
   comparing the measured excitation pattern of the basilar membrane with an expected excitation pattern based on the acoustic test signal, and
   establishing the calibration mapping by assigning characteristic frequencies to the excited positions and the electrode array.

2. The calibration method according to claim 1, wherein the sensor is a vibration sensor, an accelerometer, or an ultrasound sensor, the method comprising obtaining a frequency response from the sensor.

3. The calibration method according to claim 2, wherein the sensor comprises a plurality of sub-sensors arranged along a length of the cochlea implant, the method comprises obtaining from each of the sub-sensors a signal in response to the acoustic signal, and the step of establishing the mapping includes mapping the response at each of the sub-sensor's position.

4. The calibration method according to claim 2, wherein the hearing system comprises a processor for processing an input signal and the method includes calibrating the input signal using the processor before applying the processed signal to the electrode array.

5. The calibration method according to claim 2, wherein the electrode array is distributed evenly over a length of the lead.

6. The calibration method according to claim 2, wherein the plurality of sensors are distributed among the electrodes of the electrode array.

7. The calibration method according to claim 1, wherein the sensor comprises a plurality of sub-sensors arranged along a length of the cochlea implant, the method comprises obtaining from each of the sub-sensors a signal in response to the acoustic signal, and the step of establishing the mapping includes mapping the response of at each of the sub-sensor's position.

8. The calibration method according to claim 7, wherein the hearing system comprises a processor for processing an input signal and the method includes calibrating the input signal using the processor before applying the processed signal to the electrode array.

9. The calibration method according to claim 7, wherein the electrode array is distributed evenly over a length of the lead.

10. The calibration method according to claim 7, wherein the plurality of sensors are distributed among the electrodes of the electrode array.

11. The calibration method according to claim 1, wherein the hearing system comprises a processor for processing an input signal and the method includes calibrating the input signal using the processor before applying the processed signal to the electrode array.

12. The calibration method according to claim 11, wherein the electrode array is distributed evenly over a length of the lead.

13. The calibration method according to claim 11, wherein the plurality of sensors are distributed among the electrodes of the electrode array.

14. The calibration method according to claim 1, wherein the electrode array is distributed evenly over a length of the lead.

15. The calibration method according to claim 1, wherein the plurality of sensors are distributed among the electrodes of the electrode array.

16. A hearing system including:
   an implantable housing having a lead configured to be implanted into the cochlea of a user,
   the lead including an electrode array and a plurality of sensors,
   a processor configured to receive an input signal to be presented to the user via the electrode array, the processor storing a calibration mapping that assigns characteristic frequencies to the excited positions of the electrode array relative to the cochlea when in an implanted state, the processor further configured to apply the calibration mapping cochlea so as to achieve stimulation of the cochlea according to the calibration mapping when presenting the input signal to the user, wherein the processor establishes the calibration mapping based on a calibration process comprising:
   providing acoustic stimulation in the ear canal with an acoustic test signal with known spectrum, where after the middle ear converts the acoustic test sound to mechanical excitation of the basilar membrane, which responds with motion that performs a frequency-to-place conversion,
   measuring, via the sensor in the cochlea implant, the excitation pattern of the basilar membrane,
   comparing the measured excitation pattern of the basilar membrane with an expected excitation pattern based on the acoustic test signal, and
   establishing the calibration mapping by assigning characteristic frequencies to the excited positions and the electrode array.

17. The hearing system according to claim 16, wherein the electrodes of the electrode array is distributed evenly over a length of the lead, or wherein the electrodes of the electrode array includes a one or more groups of two or more closely spaced electrodes.

18. The hearing system according to claim 16, wherein the plurality of sensors are distributed among the electrodes of the electrode array, or wherein the plurality of sensors are interleaved with the electrodes of the electrode array.

* * * * *